United States Patent [19]
Huyser et al.

[11] Patent Number: 5,843,086
[45] Date of Patent: Dec. 1, 1998

[54] THERMAL BONE CEMENT REMOVAL SYSTEM WITH TISSUE PROTECTOR

[75] Inventors: Richard F. Huyser, Kalamazoo; Dennis A. Stratton, Plainwell, both of Mich.; Bryan T. Monroe, Austin, Tex.

[73] Assignee: Stryker Corporation, Kalamazoo, Mich.

[21] Appl. No.: 902,481

[22] Filed: Jul. 29, 1997

[51] Int. Cl.$^6$ .................................................. A61B 17/56
[52] U.S. Cl. .............................................. 606/92; 606/86
[58] Field of Search ................................ 606/99, 100, 92, 606/93, 94, 95, 86, 27, 28, 29, 30, 31

[56] References Cited

U.S. PATENT DOCUMENTS

| | | | |
|---|---|---|---|
| 5,041,120 | 8/1991 | McColl et al. | 606/99 |
| 5,151,099 | 9/1992 | Young et al. | 606/27 |
| 5,462,552 | 10/1995 | Kiester | 606/92 |

*Primary Examiner*—Guy V. Tucker
*Attorney, Agent, or Firm*—Flynn, Thiel, Boutell & Tanis, P.C.

[57] ABSTRACT

An instrument assembly for removing, as single segments, a mass of previously formed thermoplastic bone cement from a bone in a patient. A first component of the assembly includes an elongate probe having a heater tip assembly provided at one end thereof. A second component of the assembly includes an electrical system for supplying electricity to the aforesaid heater tip assembly when appropriately interconnected for effecting a heating of the heater tip. A releasable connectability of the first and second components facilitates a removal of the second component only to be replaced by a third component, namely, a hammer device so that repeated impact forces can be imparted to the elongate probe and the heater tip assembly of which is embedded in the bone cement until the impact force will cause the bone cement to crack and permit a segment thereof to be removed while being fixedly coupled to the elongate probe.

29 Claims, 4 Drawing Sheets

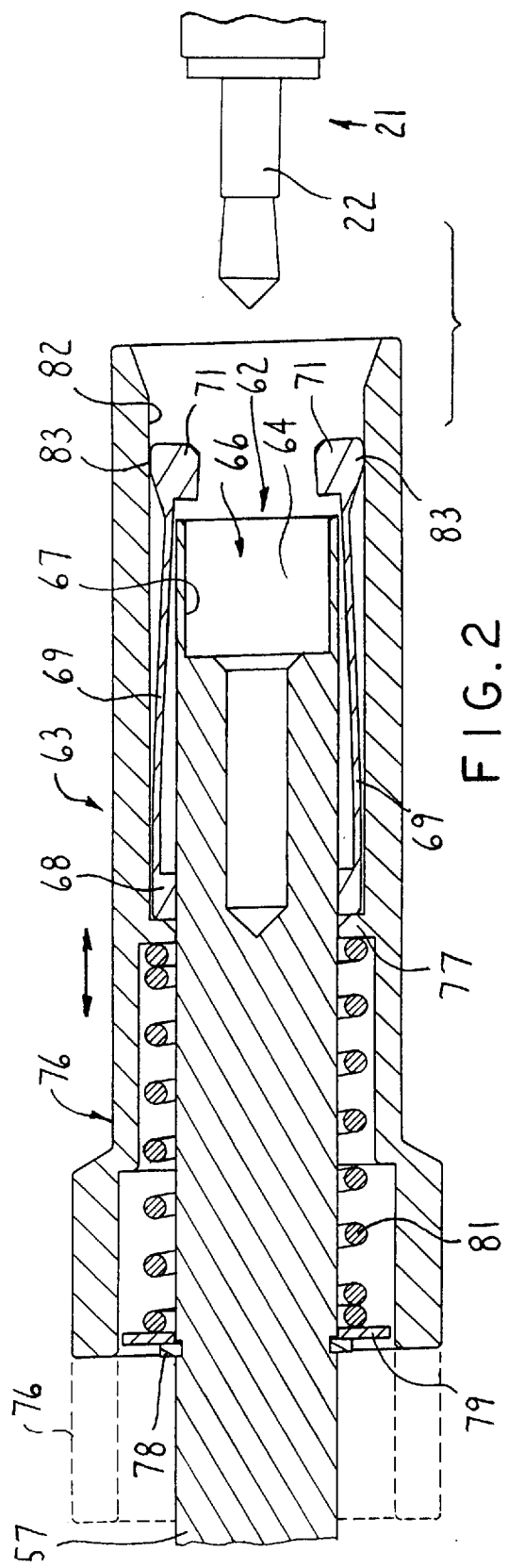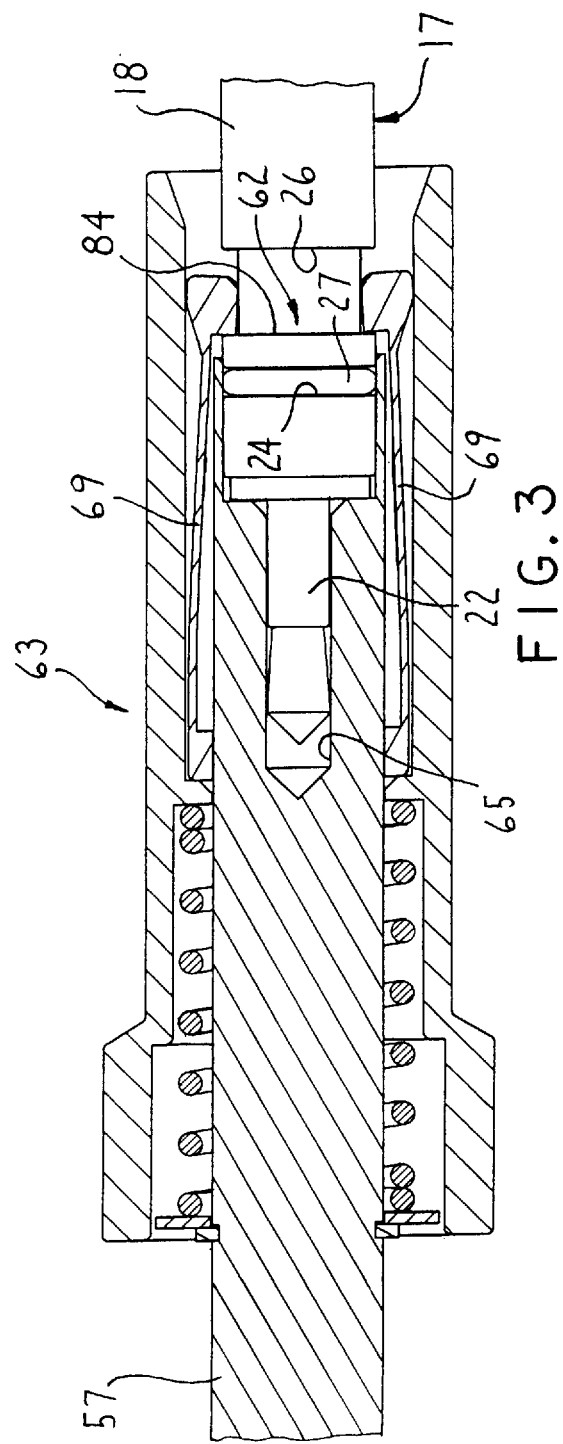

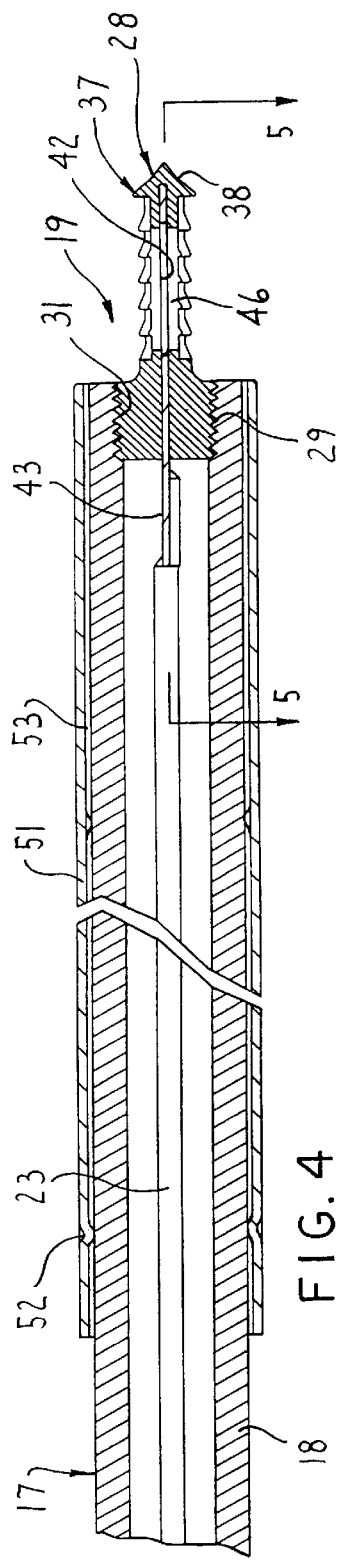
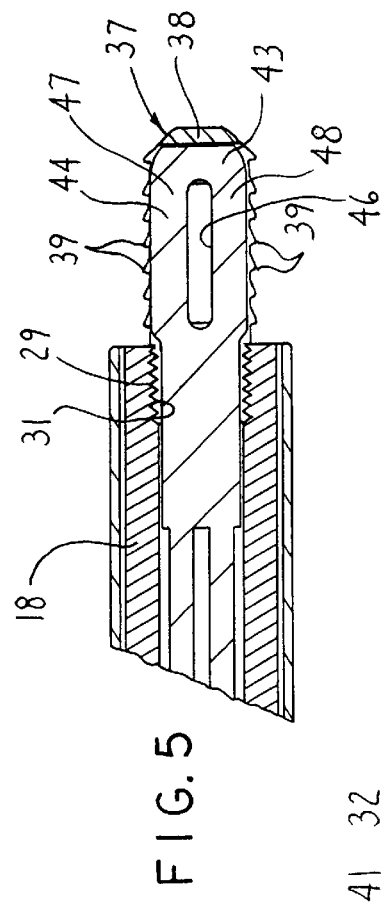
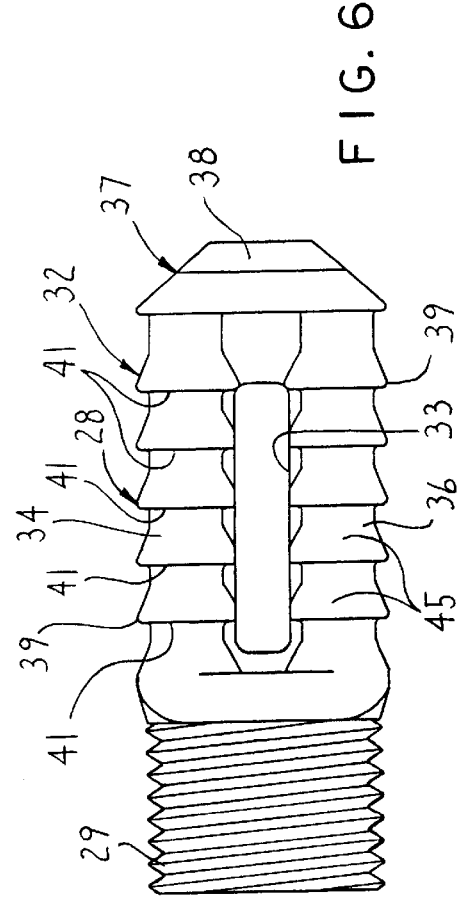

THERMAL BONE CEMENT REMOVAL SYSTEM WITH TISSUE PROTECTOR

FIELD OF THE INVENTION

This invention relates to orthopedic surgery and, more specifically, to the removal of bone cement in the repair or replacement of orthopedic prostheses.

BACKGROUND OF THE INVENTION

The invention disclosed herein is an improvement over Kiester U.S. Pat. No. 5,462,552, issued Oct. 31, 1995, reference to which is to be incorporated herein.

As is disclosed in the Kiester patent, the nature of the bone cement which is to be removed by the device disclosed herein is not critical to the invention, except that it must be thermoplastic, that is, when the cement is set in place, it must melt or soften upon the application of heat. Nearly all such cements are based on the monomer methylmethacrylate, but any other meltable cement is subject to the method described hereinafter and can be removed using the apparatus which is described herein below.

As has been recognized in the Kiester patent, it is quite common that prostheses must be removed after some period of use. Removal may be necessary because the prosthesis has loosened, because of additional or separate injury, weakening of the bone in the proximity of the cement, or any of many other conditions. The removal of cement from a previously repaired joint or from around a previously installed prosthesis presents a challenging problem to the surgeon. It is important that the cement be removed quickly, so as not to extend the time of the patient on the operating table to minimize trauma and lingering discomfort to the patient and discomfort to the surgical team.

It is, therefore, a principal feature of this invention to provide a method and an apparatus which can melt the bone cement to permit insertion of a retraction tool into the cement, allowing the retraction tool to cool in the cement and then extracting the tool and the cement.

Another object of this invention is to provide a disposable self-contained bone cement retraction instrument which can be presterilized and packaged so that no additional sterilization or further steps are required before use by the surgeon.

Another feature of the invention is the provision of an instrument, as aforesaid, which includes a bone tissue protector to minimize the amount of heat exposure to the nearby bone tissue to obviate the risks of damage to the bone and surrounding tissues.

Another feature of the invention is the provision of an instrument, as aforesaid, which is composed of separable components adapted to be conveniently and quickly releasably connected together so as to provide an easily manipulatable surgical instrument that can be introduced into the medulla region of the bone whereat the bone cement to be removed is located.

Another feature of the invention is the provision of a surgical instrument wherein the energy source for the instrument is removable and replaced with a hammer device to facilitate the application of an impact pulling force on the bone cement to facilitate in the removal of the bone cement from the medulla region of the bone.

Another feature of the invention is the provision of an instrument wherein the energy source and the hammer device, as aforesaid, are separate sterilizable components and are reusable.

Another feature of the invention is the provision of an elongate probe on the end of which is a heater tip assembly adapted to be heated to facilitate melting the bone cement to allow the heater tip assembly to be inserted into the now melted bone cement and thereafter be allowed to cool so as to result in the fixed securement of the elongate probe to the bone cement in the medulla region in the bone so that after removal the elongate probe from the patient's bone with a segment of the bone cement attached, the elongate probe with attached bone cement may be disposed of and replaced with a new elongate probe for use in association with the energy source and the hammer device as aforesaid.

SUMMARY OF THE INVENTION

The features, objects and purposes of the invention are met by providing an instrument assembly for removing, as single segments, a mass of previously formed thermoplastic bone cement from a bone in a patient. The instrument assembly includes first and second separate components with first and second coupling means for releasably and operatively coupling the two components together. The first component includes an elongate probe having a heater tip assembly provided at one end thereof and configured to be inserted into the medulla region of a bone in a patient from which a mass of thermoplastic bone cement is to be removed, the heater tip assembly including a heater tip rigidly mounted on the elongate probe at the aforesaid one end. The second component comprises an electrical system for supplying electricity to the aforesaid heater tip assembly for effecting a heating of the heater tip. The second component includes a second coupling means thereon adapted to be coupled to the first coupling means on the elongate probe so that electricity can be selectively delivered from the electrical system to the heater tip. The releasable connectability of the first and second components facilitates a removal of the second component only to be replaced by a third component, namely, a hammer device so that an impact force can be applied to the elongate probe, the heater tip assembly of which is embedded in the bone cement so that the impact force will cause the bone cement to crack and a segment thereof removed while being fixedly coupled to the elongate probe.

BRIEF DESCRIPTION OF THE DRAWINGS

Other features, objects and purposes of this invention will be apparent to persons acquainted with instruments of this general type upon reading the following specification and inspecting the accompanying drawings, in which:

FIG. 2 is an enlarged sectional view taken along the line 2—2 of FIG. 1;

FIG. 3 is a view similar to FIG. 2 but with the proximal end of the elongate probe inserted into the coupling;

FIG. 4 is a sectional view taken along the line 4—4 of FIG. 1;

FIG. 5 is a sectional view taken along the line 5—5 of FIG. 4;

FIG. 6 is an enlarged view of the heater tip; and

DETAILED DESCRIPTION

Figure 1:
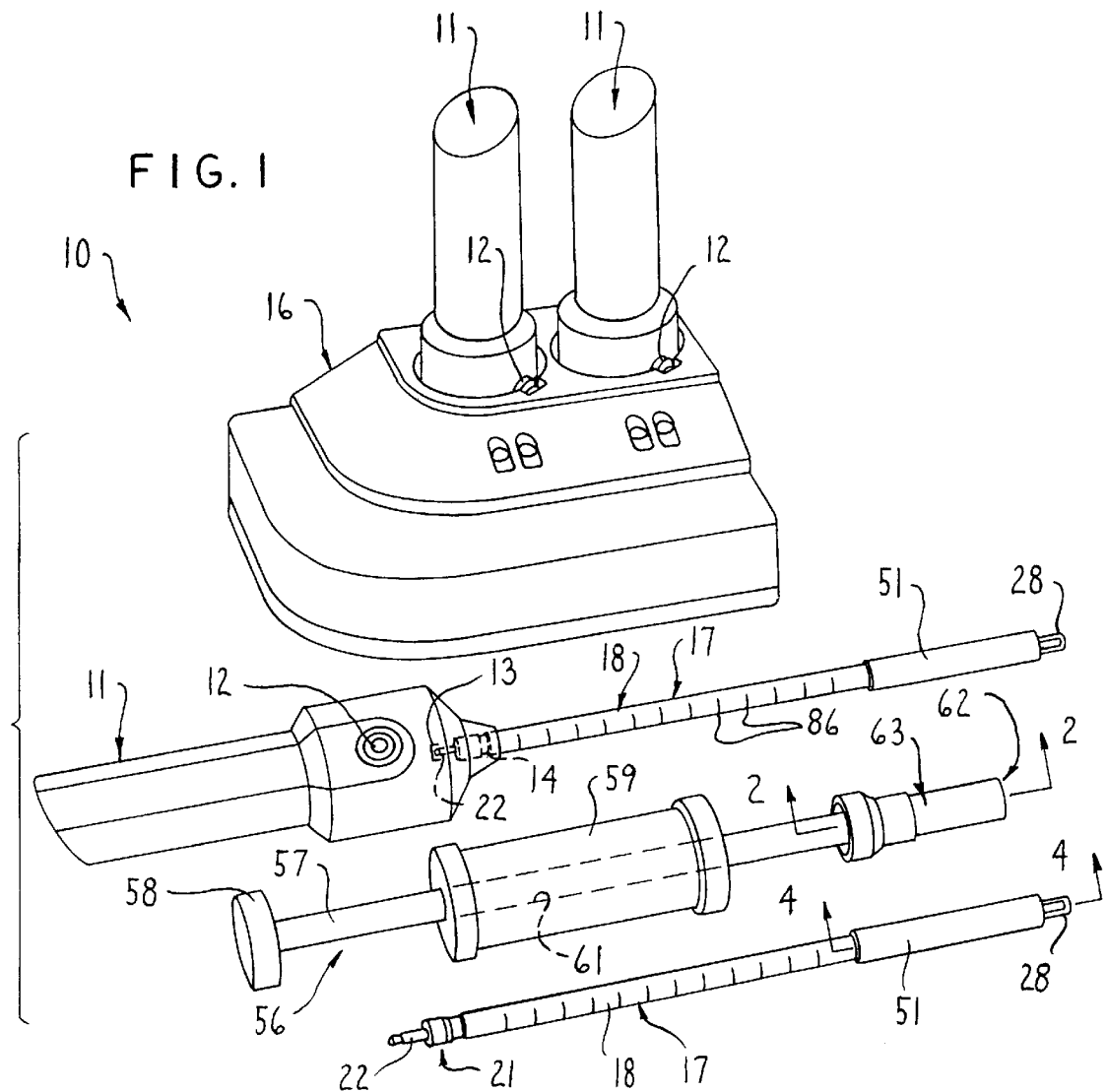
FIG. 1 is an isometric view illustrating the components of the instrument assembly.

Certain terminology will be used in the following description for convenience and reference only and will not be limiting. The words "up", "down", "right" and "left" will designate directions in the drawings to which reference is made. The words "in" and "out" will refer to directions toward and away from, respectively, the geometric center of the device and designated parts thereof. Such terminology will include derivatives and words of similar import.

FIG. 1 illustrates a cement removal system (CRS) 10 embodying the invention. Specifically, the CRS 10 includes at least one handpiece 11 containing conventional rechargeable batteries (not illustrated) and a switching device 12 for facilitating a connection of the electrical energy of the battery to an electrical contact 13 oriented in a socket 14 provided on the handpiece 11. The switch 12 is, in this particular embodiment, a push button activated switch of a conventional variety to, and as aforesaid, facilitate connection of the electrical energy of the battery to the contact 13. If desired, multiple push button activated switches can be provided on the handpiece 11, such as two of such switches, so that both push buttons thereof need to be depressed so as to effect the delivery of electrical energy from the battery to the contact 13. A base unit 16 is provided and facilitates connection from a commercially available electrical energy source to the terminals of the battery inside the handpiece to facilitate a recharging of the battery in a well-known manner. The base 16 includes a pair of sockets into which can be placed handpieces for convenient recharging of the batteries. The terminals of the batteries are accessed through the respective sockets 14 and contacts 13 in a conventional manner.

In addition to the handpiece component 11, a further component includes an elongate probe 17. In FIG. 1, one elongate probe 17 is shown connected to the handpiece 11 while the other elongate probe is free of connection with any other component. Each elongate probe 17 includes an elongate hollow cylindrical sleeve 18 having a distal end thereof, a heater tip assembly 19 and, at the other end, a coupling structure 21 which includes an electrical probe connecter 22 projecting from the proximal end. In this particular embodiment, the probe connecter 22 is forced fit into the hollow interior at the proximal end of the sleeve 18 with a sufficient force to prevent inadvertent removal thereof therefrom. A pair of electrical conducting wires 23 (only one of which is shown in FIG. 4) are electrically connected to the probe connecter at one end and to the heater tip assembly 19 at the other end so that electrical energy can be supplied therebetween. One wire is electrically connected to the electrically hot portion of the probe connecter 22 while the other wire is electrically connected to the grounded portion of probe connecter 22. The coupling structure 21 additionally includes a pair of annular grooves 24 and 26 on the peripheral surface of the sleeve 18 adjacent the probe connecter 22. A rubber O-ring 27 is provided in the groove 24 bounded by the walls of the groove. A peripheral surface of the O-ring 27 protrudes beyond the radial extremity of the outer surface of the sleeve 18. The annular groove 26 is wider than is the groove 24 for reasons that will become apparent from the further detailed description set forth below.

Figure 7:
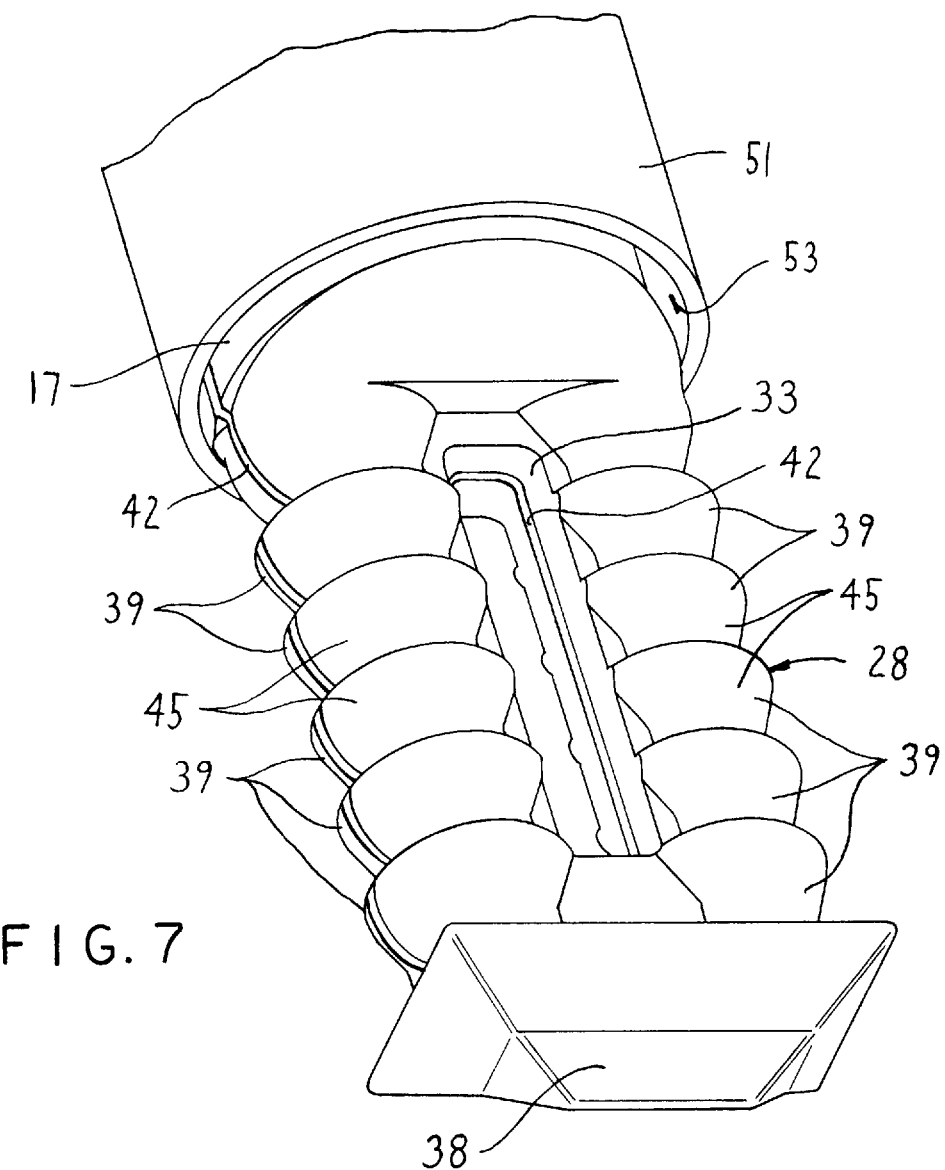
FIG. 7 is an enlarged isometric view of the heater tip located at the distal end of the elongate probe.

Referring now to the heater tip assembly 19 oriented at the distal end of the elongate probe 17, the heater tip assembly includes a heater tip 28 which includes an externally threaded end 29 which is threadedly received in an internally threaded distal end portion 31 of the sleeve 18. The heater tip 28 includes a ring-like tip 32 having a central opening 33 and a pair of elongate side members 34 and 36 that are generally parallel and are joined together at their respective distal ends 37 by a wedge-like member 38. The side members 34 and 36 each have buttressed lands 39 thereon which define flat surfaces 41 facing axially toward the external thread 29. The buttressing structure 45 is oriented on a side of the land remote from the flat surface 41. In addition, a slot 42 is provided in the heater tip 28 as best illustrated in FIG. 4. In this particular embodiment, the slot 42 opens laterally on both sides of the tip (one side of which is shown in FIG. 7) as well as into the central opening 33 and into the wedge-like member 38 at the distal end 37 of the heater tip 28. The opposing side walls of the slot 42 are parallel with one another as illustrated in FIG. 4.

An electrical resistivity element 43 is electrically connected to both of the electrical wires 23 so that electricity flowing to and from the electrical resistivity element will flow through the element to thereby heat same to a very high temperature. Heat will be conducted from the electrical resistivity element 43 to the heater tip 28 by reason of a contact of the opposing side walls of the slot 42 with the oppositely facing surfaces of the electrical resistivity element 43. It will be noted in FIG. 5 that the electrical resistivity element 43 has a ring-like distal end 44 with a central opening 46 conforming in size to the opening 33 in the heater tip 28. The lateral edges of the ringlike end 44 include side members 47 and 48 that extend coextensively with the side members 34 and 36, respectively, of the heater tip 28. As a result, heat energy formed in the ring-like electrical resistivity element 43 is conducted to the heater tip 28 by reason of the contact between the opposed surfaces in the slot 42 engaging the oppositely facing surfaces of the electrical resistivity element 43.

An elongate bone tissue protecting heat shield 51 is provided and encircles the periphery of the sleeve 18 over a region extending from the distal end of the elongate probe 17 toward the proximal end thereof. In this particular embodiment, the heat shield 51 includes a plurality of dimples 52 provided in the peripheral surface thereof which cause the material of the shield to project radially inwardly and into engagement with the peripheral surface of the sleeve 18 as best depicted in FIG. 4. The inner diameter of the heat shield 51 is greater than the external diameter of the sleeve 18 so that a gap 53 of uniform width is formed between the external surface of the sleeve 18 and the internal surface of the heat shield 51. As a result, heat conducting from the heater tip 28 to the sleeve 18 will not be exteriorly exposed to any neighboring bone tissue due to the protective encirclement of the heat shield 51. As a result, the exterior surface of the heat shield 51 will remain cool and can, if necessary, even come into contact with bone tissue without any detrimental effect thereto.

In addition to the handpiece 11 and the elongate probe 17, there is a third component in the form of a hammer device 56 illustrated in FIG. 1. The hammer device includes an elongate rod 57 having at a proximal end thereof, here the left end in FIG. 1, an enlarged striker plate 58. A weighted sleeve 59 having a central opening 61 therethrough is mounted for movement along the length of the rod 57 and into engagement with the striker plate 58. The distal end 62 of the elongate rod 57 has a coupling structure 63 thereat. Details of the coupling structure 63 are shown in FIGS. 2 and 3. The distal end 62 of the elongate rod 57 includes a pocket 66 conformed in size and shape to the proximal end of the elongate probe 17 and the probe connecter 22 so that the proximal end and probe connecter 22 can be snugly received into the pocket 66. The inner surface 67 of an enlarged segment 64 of the pocket 67 is adapted to slidingly engage the peripheral surface of the O-ring 27 as shown in FIG. 3 so as to maintain the elongate probe 17 centrally oriented within the pocket 66. The probe connecter 22 is received in a smaller segment 65 of the pocket 66.

An annular band 68 is welded onto an exterior surface of the elongate rod 57 a finite distance from the distal end 62 thereof. The band 68 has a plurality of longitudinally extending fingers 69 with fingers having enlarged heads 71 at the distal ends thereof, which heads 71 are. oriented beyond the distal end 62 of the elongate rod 57. The fingers are elastically yieldable so that the heads 71 will be permitted to move radially inwardly and outwardly.

An external sleeve 76 encircles the distal end 62 and the heads 71. An intermediate wall 77 is provided internally of the sleeve 76 and abuts against the band 68 on a side thereof remote from the fingers 69 and the head 71. A spring clip 78 is received in a corresponding groove in the peripheral surface of the elongate rod 57 and, along with a washer 79, serve as an abutment for one end of a spring 81. The other end of the spring 81 abuts against the aforementioned intermediate wall 77. As a result, a spring force of the spring 81 urges the sleeve 76 rightwardly so that intermediate wall thereof abuts against the band 68. As a result, and when the sleeve 76 is in the position illustrated in FIGS. 2 and 3, the interior surface 82 of the sleeve 76 contacts the radially outer surface 83 of the heads 71 so as to prevent the heads 71 from moving radially outwardly. However, when the sleeve 76 is moved to the left to the broken line position thereof and against the urging of the spring 81, the heads 71 will emerge from the right end of the sleeve 76 and be allowed to elastically flex radially outwardly so that the enlarged heads 71 will automatically be removed from the groove 26, especially when the elongate probe 17 is physically pulled away from the coupling structure 63. As a result, when the proximal end of the elongate probe 17 is inserted into the coupling structure 63 to the position illustrated in FIG. 3 and the sleeve 76 released so that the spring 81 will urge the sleeve 76 to the right and the position illustrated in FIGS. 2 and 3, the inner surface 82 of the sleeve 76 will slidingly engage the radially outer surface 83 of the enlarged head 71 to cause the enlarged head 71 to move radially inwardly into the groove 26 and become engaged with an axially facing surface 84 of the groove 26 so as to prevent inadvertent removal of the elongate probe 17.

In use, and assuming that the surgical site has been appropriately prepared for insertion of the aforedescribed instrument into the medulla region of the patient's bone for the purpose of removing bone cement located therein, the surgeon will first effect an insertion of the proximal end of the elongate probe 17 into the socket 14 of the handpiece 11. The O-ring 27 will facilitate the frictional holding of the elongate probe 17 in the socket 14. The probe connecter 22 will electrically connect with the contact 13 and ground connection in the socket 14 to facilitate the supply of electrical energy from the battery in the handpiece to the heater tip 28 when one or more switches 12 are selectively activated. This assumes that the handpiece has been appropriately charged by the charging circuit located in the base unit 16. The surgeon will then insert the attached elongate probe 17 into the opening in the bone to place the heater tip 28 in contact with the bone cement located in the medulla region of the patient's bone. The opening in the medulla region of the patient's bone will be sufficient to receive the maximum diameter of the heat shield 51. Thereafter, the surgeon will selectively activate the push button(s) on the switch(es) 12 to cause electrical energy to be supplied to the electrical resistivity element 43 to effect a conductive heating of the heater tip 28. Once the heater tip is appropriately heated, it can then be pushed into engagement with the bone cement causing the bone cement to melt. The wedge-like tip 38 on the heater tip 28 will facilitate the insertion of the heater tip into the now melting bone cement. Insertion can also be judged by graduation marks 86 on the exterior of the elongate sleeve 18. Once the heat shield 51 contacts the bone cement, resistance to further insertion will be felt by the surgeon and electrical energy to the heater tip can be terminated by release of the push button part of the switch (es) 12. After a period of time has passed or preferably through the use of a sterile irrigant allowing or causing the bone cement to again solidify around the heater tip 28, and into the central opening 33 thereof, the handpiece 11 can simply be pulled off from the proximal end of the elongate probe 17 and set aside for further use. The battery in the handpiece 11 is designed for use with several elongate probes, if necessary, per surgical case. Recharging of the battery, through a placement of the handpiece into the appropriate socket on the base 16, is usually to occur between surgical cases. Thereafter, the hammer device 56 can be moved into axial alignment with the elongate probe 17 and the proximal end of the elongate probe inserted into the pocket 66 in the distal end 62 of the elongate rod 57. In order to cause this to happen, the sleeve 76 must first be moved to the left in FIG. 2 against the compressive force of the spring 81 to cause the enlarged heads 71 to project beyond the distal end 62 of the sleeve 76 so that the proximal end of the elongate probe can be received into the pocket 66. After the proximal end of the elongate rod 17 has been fully inserted into the pocket 66, the sleeve 76 can be released and allowed to move to the right so that the internal surface 82 of the sleeve 76 will slidingly engage the radially outer surface 83 of the enlarged head 71 to urge the enlarged head 71 radially inwardly into the now aligned groove 26 and into engagement with the axially facing wall 84 thereof. As a result, the elongate probe 17 will be locked into engagement with the elongate rod 57 of the hammer device 56. Thereafter, the surgeon can repeatedly and rapidly slide the weight 59 away from the coupling structure 63 and into engagement of the striker plate 58 to repeatedly impart an impact force to the elongate probe 17 and the heater tip 28 fixedly connected thereto until a segment of bone cement will be broken away from the main compliment thereof and allowed to be removed from the medulla region of the patient's bone.

The elongate probe 17 with attached bone cement is to be discarded. If additional bone cement is to be removed from the medulla region of the patient's bone, the aforementioned process can be repeated but with a new elongate probe 17. Graduation marks 86 are provided on the peripheral surface of the elongate sleeve 18 so as to facilitate the surgeon's placement of the next elongate probe into the medulla region of the patient's bone for imbedding the heater tip thereof into the bone cement using the same process as has been described above. Thereafter, each previous elongate probe with the plug of bone cement embracing the heater tip thereof may be disposed of in a suitable fashion.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An instrument assembly for removing, as single segments, a mass of previously formed thermoplastic bone cement from a bone in a patient, comprising:

an assembly of first and second separate components and first and second coupling means for releasably and operatively coupling said two components together;

said first component comprising an elongate probe having proximal and distal ends, a heater tip assembly forming the distal end of the elongate probe, said heater tip assembly being constructed and configured to be inserted proximate a bone of a patient from which a mass of thermoplastic bone cement is to be removed, said heater tip assembly including an electrical heater tip rigidly mounted on said distal end of said elongate probe, and said first coupling means at said proximal end thereof;

said first coupling means including a first electrical connecter and means for conducting electricity from said first electrical connecter to said heater tip for effecting a heating of said heater tip;

said second component comprising an electrical system for supplying electricity to said heater tip assembly for effecting a heating of said heater tip, said second component having said second coupling means thereon, said second coupling means including a second electrical connecter and means for selectively conducting electricity from said electrical system to said second electrical connecter, said first and second electrical connecters being configured to be electrically coupled and uncoupled when said first and second coupling means are respectively coupled and uncoupled; and wherein said elongate probe adjacent said distal end includes an elongate sleeve encircling a finite length of said elongate probe, said sleeve being spaced from said elongate probe so as to define a finite gap between an outwardly facing surface of said elongate probe and an inwardly facing surface of said sleeve so as to isolate heat from said heater tip traveling on the surface of said elongate probe adjacent said distal end from being directly exposed to the bone of a patient.

2. The instrument assembly according to claim 1, wherein said electrical system includes a rechargeable battery.

3. The instrument assembly according to claim 2, wherein said means for selectively conducting electricity includes manually engageable switching means for facilitating an electrical connection of said battery to said second electrical connecter only in response to manual engagement of said switching means.

4. The instrument assembly according to claim 3, wherein said switching means is at least one push button switch having a push button that must be manually depressed in order to electrically connect said battery to said second electrical connecter.

5. The instrument assembly according to claim 3, wherein said switching means is a pair of push button switches each having a push button, and wherein said means for selectively conducting electricity requires that each push button must be manually depressed in order to electrically connect said battery to said second electrical connecter.

6. The instrument assembly according to claim 1, wherein said sleeve is uniformly spaced from said outwardly facing surface of said elongate probe.

7. The instrument assembly according to claim 1, wherein said sleeve includes plural circumferentially and longitudinally spaced dimples in an exterior surface thereof, an inwardly projecting surface of each of said dimple on said inwardly facing surface of said sleeve contacting said outwardly facing surface of said elongate probe to thereby minimize a conducting of heat from said elongate probe to said sleeve.

8. The instrument assembly according to claim 1, wherein an outwardly facing surface on said elongate probe includes plural longitudinally spaced marking indicating a distance to a distal end of said heater tip.

9. The instrument assembly according to claim 1, wherein said second coupling means includes a socket in which is provided said second electrical connecter, said interior wall of said socket conforming to an exterior surface of said elongate probe adjacent said first electrical connecter, and wherein said first coupling means additionally includes an elastically yieldable ring encircling said elongate probe and frictionally engaging said interior wall of said socket when said first and second electrical connecters are engaged to effect a releasable frictional coupling of said second component to said first component.

10. The instrument assembly according to claim 1, wherein said means for effecting a heating of said heater tip is an electrical resistivity element.

11. The instrument assembly according to claim 10, wherein said heater tip and said electrical resistivity element are separate components.

12. The instrument assembly according to claim 11, wherein said heater tip includes a body and means defining a cavity therein, said electrical resistivity element being received in said cavity.

13. The instrument assembly according to claim 12, wherein said means defining a cavity is a uniformly wide slot in said body opening outwardly of said body both laterally and axially toward said proximal end of said elongate probe, said electrical resistivity element being a uniformly thick plate member received in said slot with opposite facing surfaces of said plate member abutting opposing wall surfaces of said slot.

14. The instrument assembly according to claim 1, wherein said heater tip is an annular member having a central opening therethrough.

15. An instrument assembly for removing, as single segments, a mass of previously formed thermoplastic bone cement from a bone in a patient, comprising:

an assembly of first and second separate components and first and second coupling means for releasably and operatively coupling said two components together;

said first component comprising an elongate probe having proximal and distal ends, a heater tip assembly forming the distal end of the elongate probe, said heater tip assembly being constructed and configured to be inserted proximate a bone of a patient from which a mass of thermoplastic bone cement is to be removed, said heater tip assembly including an electrical heater tip rigidly mounted on said distal end of said elongate probe, and said first coupling means at said proximal end thereof;

said first coupling means including a first electrical connecter and means for conducting electricity from said first electrical connecter to said heater tip for effecting a heating of said heater tip;

said second component comprising an electrical system for supplying electricity to said heater tip assembly for effecting a heating of said heater tip, said second component having said second coupling means thereon, said second coupling means including a second electrical connecter and means for selectively conducting electricity from said electrical system to said second electrical connecter, said first and second electrical connecters being configured to be electrically coupled and uncoupled when said first and second coupling means are respectively coupled and uncoupled; and a third component separate from said first and second components, said third component including an elongate rod having thereon a striker at one end and a third coupling means at another end for releasable connection to said first coupling means when said second coupling means is disconnected therefrom, and a hammer means mounted for movement along the length of said elongate rod, when said instrument is in use, for impacting said striker, the striker being so constructed and secured as part of the instrument assembly that force applied to the striker is applied through the instrument assembly to said heater tip assembly, said hammer means being constructed and configured for applying a removal force to the striker and through the instrument to said heater tip assembly.

16. The instrument assembly according to claim 15, wherein said elongate probe includes means defining an axially facing surface facing toward said distal end thereof and said heater tip thereat, said third coupling means including plural peripherally spaced finger means for contacting said axially facing surface and around a periphery of said elongate probe and means for selectively facilitating a movement of said finger means axially past said axially facing surface and restricting a return axial movement of said finger means so as to cause said finger means to contact said axially facing surface during application of said removal force.

17. The instrument assembly according to claim 15, wherein said means for effecting a heating of said heater tip is an electrical resistivity element.

18. The instrument assembly according to claim 17, wherein said heater tip and said electrical resistivity element are separate, components.

19. The instrument assembly according to claim 18, wherein said heater tip includes a body and means defining a cavity therein, said electrical resistivity element being received in said cavity.

20. The instrument assembly according to claim 19, wherein said means defining a cavity is a uniformly wide slot in said body opening outwardly of said body both laterally and axially toward said proximal end of said elongate probe, said electrical resistivity element being a uniformly thick plate member received in said slot with opposite facing surfaces of said plate member abutting opposing wall surfaces of said slot.

21. The instrument assembly according to claim 15, wherein said heater tip is an annular member having a central opening therethrough.

22. An instrument assembly for removing, as single segments, a mass of previously formed thermoplastic bone cement from a bone in a patient, comprising:

an assembly of first and second separate components and first and second coupling means for releasably and operatively coupling said two components together;

said first component comprising an elongate probe having proximal and distal ends, a heater tip assembly forming the distal end of the elongate probe, said heater tip assembly being constructed and configured to be inserted proximate a bone of a patient from which a mass of thermoplastic bone cement is to be removed, said heater tip assembly including an electrical heater tip rigidly mounted on said distal end of said elongate probe, and said first coupling means at said proximal end thereof;

said first coupling means including a first electrical connecter and means for conducting electricity from said first electrical connecter to said heater tip for effecting a heating of said heater tip;

said second component comprising an electrical system for supplying electricity to said heater tip assembly for effecting a heating of said heater tip, said second component having said second coupling means thereon, said second coupling means including a second electrical connecter and means for selectively conducting electricity from said electrical system to said second electrical connecter, said first and second electrical connecters being configured to be electrically coupled and uncoupled when said first and second coupling means are respectively coupled and uncoupled; and wherein said heater tip includes a wedge surface means at a distal end thereof to facilitate a forced insertion of a heated heater tip into the thermoplastic bone cement melted by contact with a heated said heater tip.

23. The instrument assembly according to claim 22, wherein said heater tip is an annular member having a central opening therethrough, melted thermoplastic bone cement flowing into said opening and resolidifying when said heater tip is allowed to cool by discontinuing a supply of electricity to said heater tip assembly.

24. The instrument assembly according to claim 23, wherein an outer surface of said heater tip includes surface means for facilitating an insertion of said heater tip in a first direction into said thermoplastic bone cement when melted and simultaneously resisting withdrawal thereof from said thermoplastic bone cement when said heater tip is urged in a second direction opposite to said first direction.

25. The instrument assembly according to claim 22, wherein said means for effecting a heating of said heater tip is an electrical resistivity element.

26. The instrument assembly according to claim 25, wherein said heater tip and said electrical resistivity element are separate components.

27. The instrument assembly according to claim 26, wherein said heater tip includes a body and means defining a cavity therein, said electrical resistivity element being received in said cavity.

28. The instrument assembly according to claim 27, wherein said means defining a cavity is a uniformly wide slot in said body opening outwardly of said body both laterally and axially toward said proximal end of said elongate probe, said electrical resistivity element being a uniformly thick plate member received in said slot with opposite facing surfaces of said plate member abutting opposing wall surfaces of said slot.

29. The instrument assembly according to claim 22, wherein said heater tip is an annular member having a central opening therethrough.

* * * * *